United States Patent [19]

Ansorge et al.

[11] Patent Number: 5,137,698
[45] Date of Patent: Aug. 11, 1992

[54] APPARATUS FOR CARRYING OUT CHEMICAL REACTION SEQUENCES

[75] Inventors: Wilhelm Ansorge, Gaiberg/Heidelberg; Christian Schwager, Limburgerhof; Brian Sproat, Heidelberg, all of Fed. Rep. of Germany

[73] Assignee: Europäisches Laboratorium für Molekularbiologie (EMBL), Heidelberg, Fed. Rep. of Germany

[21] Appl. No.: 449,903

[22] PCT Filed: Apr. 24, 1989

[86] PCT No.: PCT/EP89/00447
§ 371 Date: Jan. 16, 1990
§ 102(e) Date: Jan. 16, 1990

[87] PCT Pub. No.: WO89/10188
PCT Pub. Date: Nov. 2, 1989

[30] Foreign Application Priority Data

Apr. 22, 1988 [DE] Fed. Rep. of Germany ....... 3813671

[51] Int. Cl.$^5$ ............................ B01J 3/00; B01J 19/24; C12M 1/00
[52] U.S. Cl. ..................................... 422/242; 422/116; 422/131; 422/237; 422/238; 435/287; 935/88
[58] Field of Search ............... 422/236, 237, 238, 149, 422/155, 189, 104, 310, 131, 103, 116, 242; 935/88; 210/489, 498; 435/287

[56] References Cited

U.S. PATENT DOCUMENTS 4,187,077 2/1980 Covington et al. ................ 622/104
4,728,502 3/1988 Hamill .............................. 935/88 X

FOREIGN PATENT DOCUMENTS

164206 12/1985 European Pat. Off. .
181491 5/1986 European Pat. Off. .

*Primary Examiner*—James C. Housel
*Assistant Examiner*—William Chan
*Attorney, Agent, or Firm*—Akoo-Toren

[57] ABSTRACT

An apparatus for carrying out chemical reaction sequences includes a stack of reaction plates arranged one above another and displaceable according to choice step by step in relation to one another, which are provided with passages arranged at the stepping interval, one of which passes in each case is formed as reaction chamber. A plate displacement device serves for the displacement of the respective plate, according to choice, in relation to the remaining plate stack. A pressure application part of a clamping device is provided with a faculty for movement of the plates in relation to one another between a pressure application position with sealing clamping together of the plates and a release position. A force transmission device in the form of a two-armed lever couples the plate displacement device with the pressure application part, so that on a movement of the plate displacement device beyond one of the two outer plate displacement positions into an end position the pressure application part is moved into the pressure application position.

21 Claims, 5 Drawing Sheets

APPARATUS FOR CARRYING OUT CHEMICAL REACTION SEQUENCES

BACKGROUND OF THE INVENTION

The invention relates to an apparatus for carrying out chemical reaction sequences, having a stack of reaction plates arranged one above another and optionally displaceably in relation to one another step by step in a direction of displacement perpendicular to the stacking direction, which plates are provided with passages arranged at the stepping interval, one of which in each case is formed as reaction chamber, a plate displacement device for the optional displacement of the respective plate in relation to the remaining plate stack by means of a plate displacement part drivable according to choice, which is movably mounted on a head of the plate displacement device which is movable according to choice in the stack direction between pate displacement positions allocated to the individual plates, and a tightening device having a presser part acting on the plate stack, which presser part is movable between a pressure application position with sealing clamping together of the plates and a release position with possibility of movement of the plates in relation to one another.

An apparatus of this kind is known (EP-A-164,206). With it it is possible simultaneously to carry out a series of biochemical reactions, especially the synthesis of DNA fragments, as also known per se from EP-A-181,491, using a stack of plates of circular disc form which can be rotated manually in relation to one another. The bases A, C, G, T are fed to the stack by way of four passages. According to the desired sequence the reaction chamber of the respective plate is brought into alignment with the passage delivering the desired base. The apparatus known from the initially mentioned EP-A-164,206 permits an automatic displacement (rotation) of the individual plates in relation to one another, so that a plurality, corresponding to the number of plates, of simultaneous synthesis reactions can be carried out with a high number of reaction steps in computer-supported manner without manual intervention. However in this known solution the apparatus expense is considerable. In all four drive systems are necessary: a height drive which drives a drive spindle for the height adjustment of the plate displacement device and a drive spindle for a shift lock a drive as part of the plate displacement device, which brings a plate displacement part in the form of a presser roller drivable according to choice by means of a further drive into and out of engagement with the external circumference of the respective plate; a fourth drive in the form of a lifting cylinder which serves for the movement of the presser part in the form of a plate. This plate is arranged above the plate stack and is movable between the release position, in which the plates are rotatable in relation to one another for the preparation of the next reaction, and the pressure application position, in which the plates are pressed together in sealing manner by the pressure application part. The reaction step in each case is carried out in the pressure application position.

SUMMARY OF THE INVENTION

In contrast thereto the problem of the invention consists in preparing an apparatus of the initially stated kind, with simplified construction and reliable function.

This problem is solved in that the clamping device comprises a force-transmission device coupled with the presser part, on which device the plate displacement device acts for the movement of the presser part out of the release position into the pressure application position on a movement of the head of the plate displacement device beyond one of the two outer plate displacement positions into an end position.

Thus in accordance with the invention the pressure application part is actuated by the plate displacement device so that a separate drive system for the pressure application part can be eliminated.

An especially simple form of construction in accordance with the invention is characterised in that the force-transmission device comprises a two-armed lever, one end of which co-operates with the plate displacement device and the other end with the pressure application part. Thus the two-armed lever transmits the upward movement of the plate displacement device, with sign reversal, to the pressure application part to be moved downwards.

For the precise adjustment of clamping pressure, for example after change of the number of reaction plates, it is proposed that at least one of the ends of the two-armed lever is provided with a clamping pressure adjustment device. It is preferredly provided here that the clamping pressure adjustment device is formed by an adjustable double wedge.

In the known apparatus as named at the outset a shift lock (in the form of the threaded spindle 63) movable in the stack direction with the plate displacement device is provided which blocks that plate directly above the plate approached by the plate displacement device in each case, in that this plate is pushed correspondingly far from above into mutually aligned passage bores of the plates. Each plate is provided with a row of passage bores of this kind spaced from one another according to the step interval. It is disadvantageous in this arrangement that the plate arranged beneath the plate to be displaced is not fixed, so that an uncontrolled accompanying rotation cf this plate can occur. If this accompanying rotation is not corrected, then in the next reaction a wrong reaction may possibly be executed in this plate. An only partial accompanying rotation of this plate would be still more unfavourable, since then all passages through this plate might possibly be blocked.

Alternatively or in addition to the above-described measures in accordance with the invention, to increase the operational reliability of the apparatus of the kind as initially stated, with simple construction, it is proposed that the shift lock also acts in blocking manner upon the plate immediately below the plate approached by the plate displacement device.

To simplify the mechanical assembly, especially by the elimination of the spindle drive in the known apparatus, it is proposed that an engagement element co-operating with counter-engagement elements arranged on the plates is rigidly arranged on the head both above and below the plate displacement part.

In order, again in a constructionally simple manner, to ensure a reliable fixing of the respective plates in all their possible positions in displacement, it is proposed that one of the elements, engagement element and counter-engagement element, comprises an engagement projection, and that the other element comprises a plurality of engagement grooves arranged side by side in the displacement direction at the step interval, extending parallel to the stacking direction and adapted in cross-section to the engagement projection.

Alternatively it can however also be provided that one of the elements, engagement element and counter-engagement element, comprises an engagement groove extending parallel with the stacking direction, and that the other element comprises several engagement projections arranged side by side in the displacement direction at the step interval and adapted to the groove cross-section.

In the case of formation of the apparatus according to the invention with a pressure application part arranged at the upper stack end it is proposed to form this with an engagement groove for the upper engagement projection of the head.

According to a further embodiment of the invention it is proposed that the plate displacement part is formed by a displacement projection movable in the displacement direction, which projection co-operates with counter-projections formed on the plates. It is especially preferredly provided in this case that the displacement projection, in an intermediate position of the plate displacement device between successive plate displacement positions, is freely movable through between the counter-projections of successive plates. This has the great advantage that the drive 75 for the horizontal movement of the head into and out of engagement with the plate stack, necessary in the known apparatus, can be eliminated.

For the sake of simplicity it can be provided here that the displacement projection and/or the counter projections are of pin form.

In normal operation with a moderate number of plates, for example 10 plates, there is no need to fear that the one or the other plate will jam in displacement. If nonetheless such jamming should occur, which can happen especially in the case of a high number of plates, it is proposed that the plate displacement apparatus is provided with an overload safety device.

Such an overload safety device, distinguished by simple structure and reliable function, is characterised according to the invention in that the plate displacement part of pin form is made electrically conductive, in that an initial stress spring, in a normal position of the plate displacement part, presses the plate displacement part against an insulating part, and in that on overloading the plate displacement part slides away from the insulating part and is pressed by the initial stress spring against an electrically conductive contact plate.

In order, even in the case of relatively slight clamping-together pressure, to ensure a reliable sealing of the passages in the transition region of successive plates, O-ring seals are proposed between successive plates.

BRIEF DESCRIPTION OF THE DRAWINGS

The invention will be explained hereinafter by a preferred example of embodiment with reference to the drawing, wherein.

DETAILED DESCRIPTION OF THE PREFERRED EMBODIMENTS

The apparatus according to the invention, designated by 10 in the Figures, serves for the simultaneous execution of several chemical reaction sequences. The use of the apparatus is especially preferred in the field of biochemical reaction chains, especially the simultaneous synthesis of several DNA lengths, even of different structures. The apparatus 10 comprises a stack 12 of reaction plates 14 lying against one another, which are arranged vertically one above another in the example of embodiment as illustrated. In principle however another stacking direction, for example in a horizontal plane, is also conceivable. A plate 14 is allocated to each reaction chain (DNA length).

Figure 4:
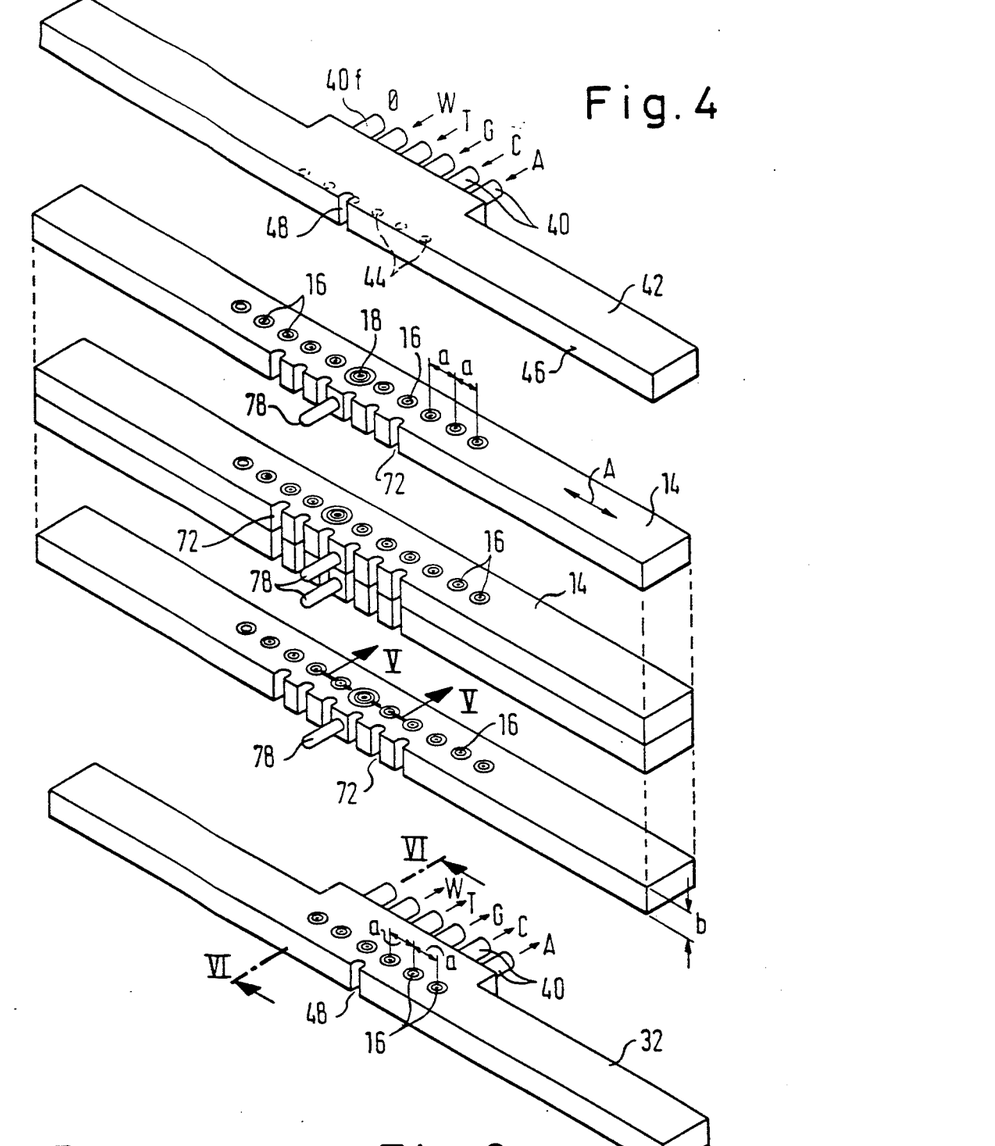
FIG. 4 shows an exploded illustration of the reaction plates of the apparatus according to FIGS. 1 to 3.
Figure 5:
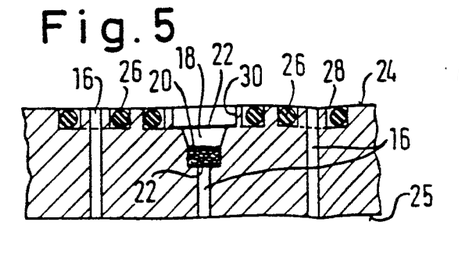
FIG. 5 shows a section along the line V—V in FIG. 4.

For the execution of the desired reaction the plate in each case is provided with a series of passages 16, one of which is formed with a widening serving as reaction chamber 18, as shown by FIGS. 4 and 5. The reaction chamber 18 can be filled with abutment bodies 20, for example in the form of small glass spheres (in English "beads") and a sieve plate 22 at the lower end and preferably also at the upper end of the reaction chamber 18 preclude escape of the abutment bodies from the reaction chamber 18.

On the plate upper side 24 in each case there are O-ring seals in the form of O-rings 26, which are inserted into ring grooves 28. These ring grooves 28 serve for sealing the passages 16 radially outwards when the plate upper side 24 is in abutment on the plate under side 25 of the next succeeding plate. The ring grooves 28 therefore encircle the passages 16 concentrically with slight spacing; one of the ring grooves has a larger diameter, namely the ring groove serving for the sealing of the reaction chamber 18, since the reaction chamber 18 merges upwards into a widening 30 which opens into the plate upper side 24.

Figure 6:
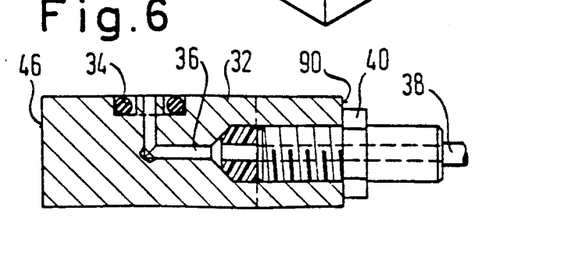
FIG. 6 shows a section along the line VI—VI in FIG. 4.

Accordingly an attachment plate 32 downwardly adjoining the plate stack 12 is provided on its upper side with O-ring seals (O-ring 34 in FIG. 6), which serve for the sealing each of one of a total of six passages 36. While the passages 16 extend vertically, the channels 36 are angled off in order to render possible a horizontal connection of drain conduits 38. In FIG. 6 there may be seen a conduit connection piece 40 screwed horizontally into the attachment plate 32.

To the lower attachment plate 32 there corresponds an upper attachment plate 42, again with six horizontal attachment pieces 40 to which six angled-off passages are connected with outlet openings 44, indicated in chain lines in FIG. 4, on the plate under side. Both attachment parts 32 and 42 are provided, in the middle of their length on the vertical longitudinal side 46 lying opposite to the attachment pieces 40, with a vertically extending groove 48, into which a lower and an upper engagement projection 50 and 52 respectively of pin form can penetrate. These projections 50 and 52 are fixedly fitted on a vertically displaceable head 54 of a plate displacement device 56 (see FIGS. 2 and 3). Regarding the passages 16 and 36 it is also to be added that these are arranged at equal distance and in the same width position each on a line on the plates 14, 32 and 42, so that in the case of appropriate mutual orientation of the plates 32, 14 and 42 the passages can be brought into mutual alignment. On a displacement of the one or the other plate 14 in relation to the other plates in the plate longitudinal direction A by a distance a, which corresponds to the axial interval of mutually immediately successive passages 16, then by reason of this uniform passage pattern again an aligned arrangement of a part of the passages of the plate just displaced with passages of the plates 14, 32 and 42, upwardly and downwardly following this plate, takes place.

The plates 32 and 42 are provided with passages 36, according to the number of the different reaction fluids. In the present example four connections are needed for the four bases A, G, C and T. A further channel serves for the feed of auxiliary fluids, as for example washing fluid. In FIG. 4 accordingly feed arrows are entered with A, C, G, T and W. An outer channel (arrow 0) can remain uncharged and then defines a parking position for the reaction chambers 18 of the plates 14. There result n connections in all (n=6) with correspondingly six attachment parts 40 in the plate 42 and in the plate 32. If necessary still further attachments can also be provided.

In contrast thereto the plates 14 are provided each with a total of m passages 16 ($m = 2n - 1 = 11$), while the middle passage is widened to the passage chamber 18. The reaction chamber 18 in each case can accordingly be brought into alignment according to choice with any one of the six connections of the plates 32 and 42, while one of the other passages 16 is also always in alignment with all the other connections. Accordingly appropriate fluid can always be fed through the six attachment parts 40 of the upper plate 42, conducted through the passages 16 of the plates 14 of the plate stack 12 to the lower plate 32 and drained away through the lower attachment parts 40.

The reaction chamber 18 of any desired plate 14 can be brought into contact according to choice with one of the fluids A, C, G, T or W, or into a parking position in alignment with the attachment placed farthest left in FIG. 4 (attachment part 40f).

Figure 1:
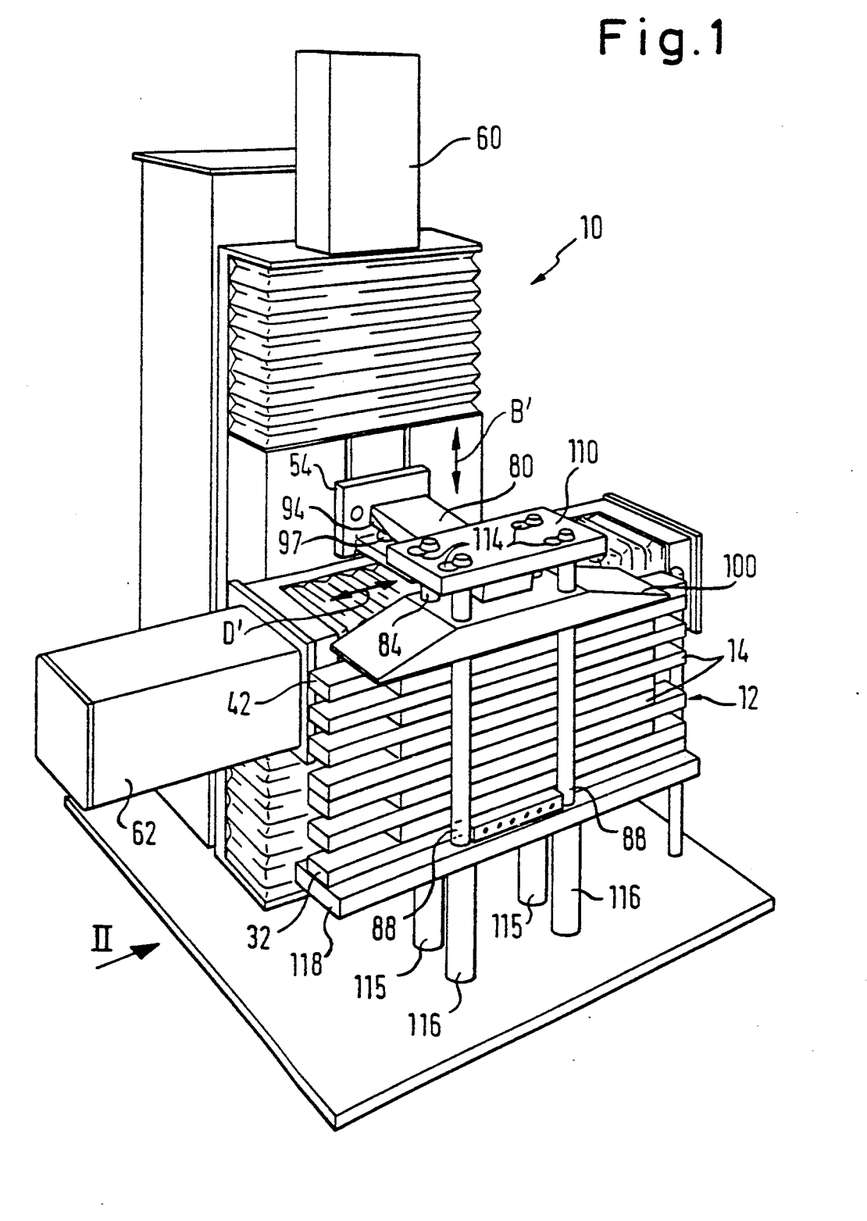
FIG. 1 shows a simplified isometric overall view of the apparatus according to the invention.
Figure 2:
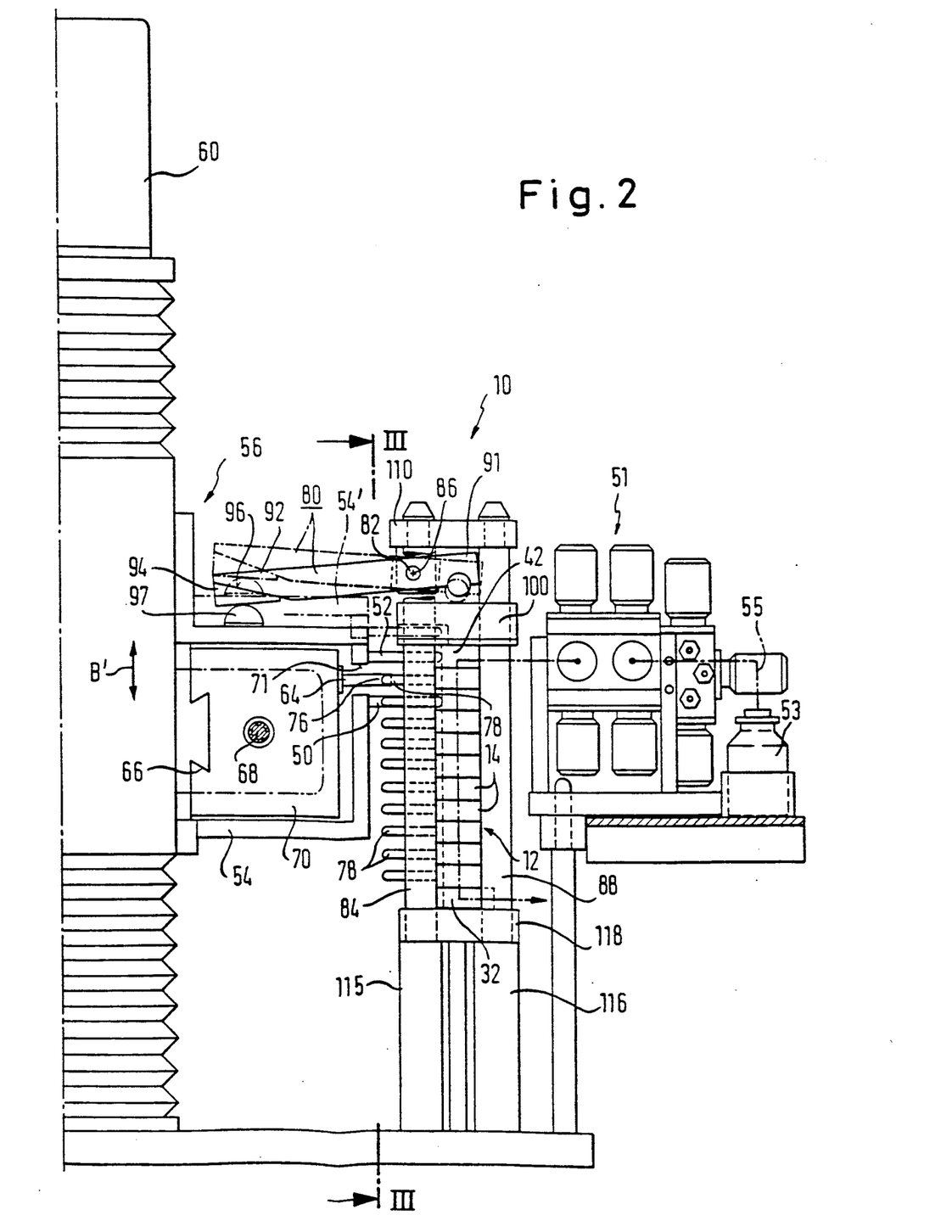
FIG. 2 shows a lateral elevation of the arrangement in FIG. 1 (seen in the direction II)

In FIG. 1 the supply leads to the plate 42 and the discharge leads 38 are omitted, likewise a pertinent valve block with reserve bottles. In FIG. 2 on the other hand the valve block is represented diagrammatically and designated by 51. Furthermore there is seen a reserve bottle 53 of the five reserve bottles at least. The fluid flow from the reserve bottle 53 into the valve block 51 and further into the upper plate 42, then through the plate stack 12 down to the lower plate 32, is indicated by a dot-and-dash line 55. Then the fluid is either returned or fed to a collecting vessel.

The valve block 51 can also be formed with a directional control valve 2/1, where a first fluid is fed to the one of the two entries and a second fluid is fed to the other of the two entries. Now according to choice either only the one or only the other or a mixture of both fluid with pre-determined mixture ratio can be supplied through the one outlet, and in the latter case the valve is switched over at short time intervals (after the style of a flip-flop element). The mixture ratio is then defined by the ratio of the times of sojourn of the valve in the two control positions. This directional control valve 2/1 can naturally also be realised by two simple change-over valves which open into a common outlet conduit and are opened alternately, so that either the one or the other fluid is fed to the common outlet conduit.

In order to obtain the desired fluid pressure, so that the fluids flow through the stack 12, in the usual way a pressure charging of the bottles 53 with pressure gas can take place. It is also possible for fluid pumps, such for example as quantity-regulating syringes, to be used for exact volume addition.

The plate displacement device 46 includes the already mentioned head 54, which is movable to and fro in the vertical direction B' with the aid of a drive (not represented further) with drive motor 60 arranged at the top. The head 54 again carries a horizontal drive system (not illustrated further) with lateral drive motor 62 for the optional horizontal displacement (arrow D' in FIG. 1) of a plate displacement part 64 of pin form. In FIG. 2 a dovetail guide 66 is indicated between herd 54 and a guide part 70 carrying the plate displacement part 64 and displaceable to and fro in relation to the head 54 by means of a threaded spindle 68. In the region of the plate displacement part 64 the head 54, which encloses the part 70 in housing manner, is provided with a passage slot 71. The plate displacement part 64 protrudes in the horizontal direction from the slot 71 and thus extends parallel with and at the equal vertical distance from the two engagement projections 50 and 52 of pin form. The distance between the plate displacement part 64 of pin form and the engagement projections 50 and 52 corresponds in each case to the thickness b of the plates 14, 32 and 42, so that when the plate displacement part 64 stands opposite to a plate 14, the two engagement projections 50 and 52 lie opposite to the next succeeding lower and upper plates 14 and/or 32 and/or 42.

The two engagement projections 50 and 52 of pin form serve for the momentary fixing of the plates 14 on both sides of the plate 14 to be momentarily displaced by the plate displacement part 64 of pin form, in order to bring the reaction chamber 18 of this plate into the current of another of the available fluids or into the parking position.

For this purpose all the plates 14 are provided with grooves 72 corresponding to the grooves 48. Since each plate 14, as already explained, can assume a total of six displacement positions in the pattern of the hole intervals a, accordingly each plate 14 is formed with a total of six of these grooves 42 with mutual groove interval a. In each of the six displacement positions one of these grooves 72 is in alignment with the two grooves 48 of the lower and upper plates 32 and 42. If all the plates 14 are situated in one of their displacement positions, then the head 54 can be driven upwards or downwards without hindrance, the two free ends of the engagement projections 50 and 52 of pin form being moved upwards or downwards within this total groove formed by the mutually aligned grooves 48, 72.

For the displacement of one of the plates 14 the head 54 is driven into the corresponding height position, so that the plate displacement part 64 of pin form lies opposite to the desired plate 14. The two engagement elements 50 and 52 then engage in blocking manner in the groove 72 of the two plates on both sides of the plate to be displaced. For the movement of this plate the plate displacement part is brought with its free end, serving as shift projection 76, to abut laterally on a counter-projection 78 of pin form, which protrudes horizontally from the opposite plate 14. Then the desired lateral displacement of the plate 14 by once or more times the distance a takes place.

In order that the same plate 14 may also be shifted in the opposite direction, the displacement projection 76, in an intermediate position of the head 54 at the level of the surface of contact of successive plates, is moved past the counter-projection 76, above or below it. Then the head 54 drives into the desired height position, so that then the displacement projection 78 can shift the counter-projection 76 in the desired counter-direction.

So that the displacement projection 76 can be moved in the horizontal direction through between the counter-projections 78 of successive plates (in the said intermediate position of the head 54), the pin diameter of the counter-projections 78 and of the displacement projection 76 is smaller than half the plate thickness b.

In order, after plate displacement has taken place, in the subsequent charging of the six through-passing channels to ensure a satisfactory sealing of these channels to the exterior, that is an adequate sealing by the O-rings 26, 34 of the O-ring seals between all plates 14, 32 and 42), these plates are clamped together in the stacking direction (vertical direction B') with the aid of a two-armed lever 80. This two-armed lever is mounted rotatably by means of a bearing shaft 82 on two forward columns 84 with horizontal pivot axis 86. The two columns 84 form a forward guide for the plates 14 with abutment of the plate fronts 46 on the columns 84. Rear columns 88 accordingly lie against the plate backs 90. In order to obtain a high initial stress force in the case of relatively slight actuation force, the arm 91 of the two-armed lever 80 pressing upon the plate stack is made with substantially shorter effective length than the other arm 92 to be actuated by the head 54.

For the precise lever adjustment and thus also for the setting of the desired initial stress force, the arm 80 is formed with a kind of double wedge. One part 94 is displaceable along a wedge face 96 of the arm 92 and fixable in the desired position. A hemispherical part 97 secured to the head 54 strikes upon the wedge 94, as soon as the head 54 is displaced upwards beyond the first plate displacement position. In the uppermost plate displacement position the shift projections 76 lies at the same level as the counter-projection 78 of the uppermost plate 14. In this position the upper engagement projection 52 is situated in the groove of the plate 42. In the subsequent movement of the head 54 further upwards into an upper end position (indicated in FIG. 2 with a dot-and-dash line and designated by 54'), the upper engagement projection 52 penetrates into a groove 98, arranged accordingly in vertical alignment, of a pressure application part 100 resting on the plate 42. At the same time the pressure application part 100 moves slightly downwards, under the action of the two-armed lever 80, so that the plate stack 12 is correspondingly compressed. The vertical groove length of the groove 98 is accordingly large.

After reaction has taken place, for the subsequent plate displacement the head 54 is driven downwards again, so that the two-armed lever 80 becomes free and the plates 14 again lie loosely one upon another. Thus they can again be displaced laterally.

Figure 3:
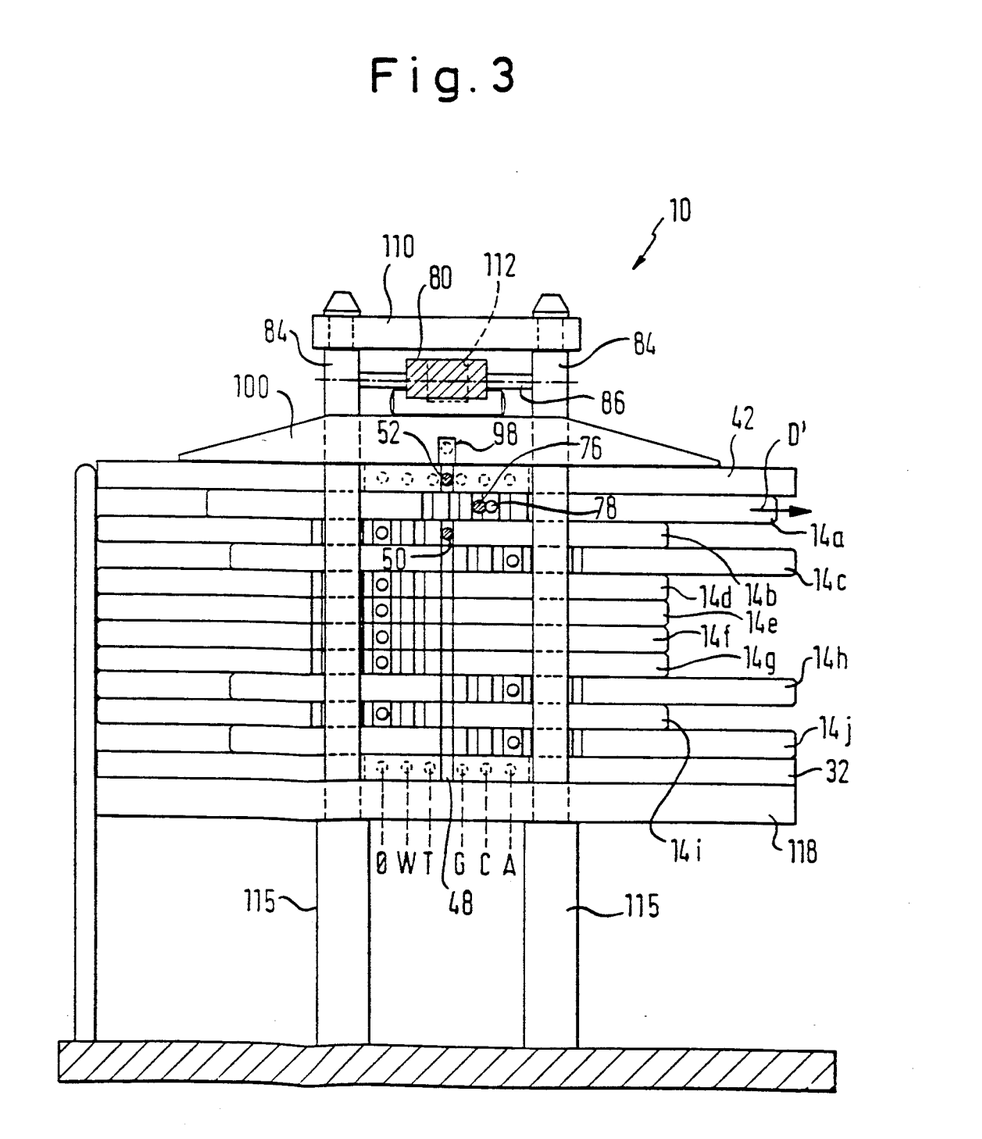
FIG. 3 shows a section along the line III—III in FIG. 2.

In the arrangement according to FIG. 3 the first plate 14a is momentarily shifted into its position placed furthest to the right (arrow D'), so that then its reaction chamber is penetrated in the next succeeding reaction by a fluid with the base A. The next following plate 14b is in the parking position; the next following plate 14c is again in the position allocated to the base A; the next following plates 14c to 14g are in the parking position, as also the plate i. The plates 14h and 14j are situated in the position allocated to the base A.

Regarding the mounting of the two-armed lever 80 it should also be mentioned that alternatively it is also possible to mount this rotatably on a head plate 110, penetrated by four columns 84 and 88, in the region of the upper column ends; a bearing bracket engaging in the double-armed lever 80 and rigidly secured to the plate 110 is indicated in FIG. 3 with a dotted outline and designated by 112. As may further be seen from FIG. 1, the plate 110 can be made fast in each case by way of a keyhole connection 114 on the upper ends of the columns 84, 88.

For the retention of the stack 12 at working level in front of the height adjustment device 56, the columns 84, 88 can be of stepped formation with lower sections 115, 116 of enlarged diameter. On the stepped annular face at the upper ends of the sections 115, 116 there rests a support plate 118, on to which again the plate stack 12 is set.

Figure 7:
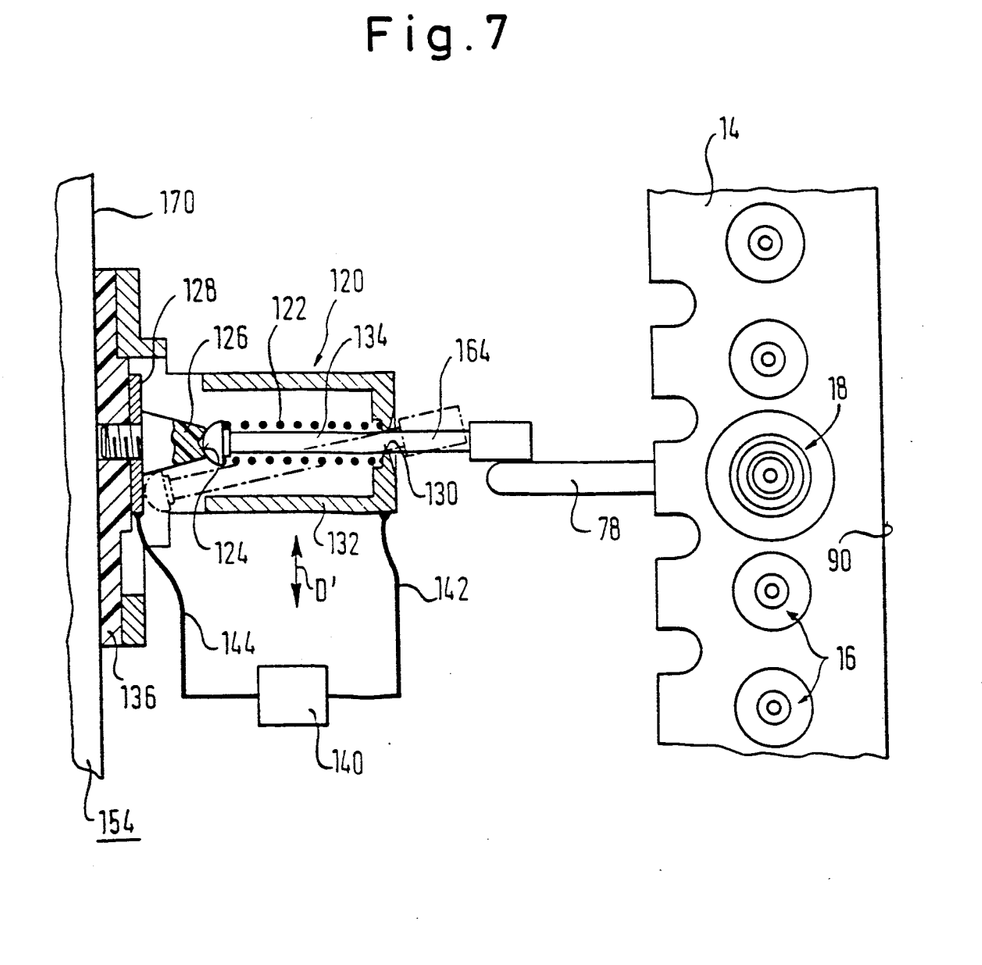
FIG. 7 shows a detail view of a modified form of embodiment of the invention in the region of the plate displacement part of pin form, with overload safety device.

When the clamping device (two-armed lever 80) is released, the plates 14 can readily be shifted laterally in the manner as described, since the weight of the plate stack, with the number as illustrated, is not yet excessively high (plates 14, especially of synthetic plastics material). The O-rings 26, 34 protruding slightly beyond the upper side 24 of the plate in each case in the relaxed condition prevent the plates from "sucking fast" to one another. In extreme cases or even in the case of a higher number of plates, under some circumstances blocking of the particular plate to be shifted can nonetheless occur. In order to prevent damage to the apparatus in this case, according to FIG. 7 an overload safety device 120 can be provided. This is formed by the plate displacement part 164 of pin form, which is made electrically conductive and is pressed by a spiral initial stress spring 122 against a concave seating 124 of an insulating part 126. The insulating part 126 is rigidly secured to the head 154. The insulating part 126 stands away from a contact plate 128 of circular disc form. The shank of the plate displacement part 126 of pin form between the two thickened ends is guided for displacement and to a certain degree tiltably in a guide opening 130 of a housing 132 protruding from the head 154, and there is an electrically conductive connection between the shank 134 and the housing 132 for the one part by way of the marginal contact of the shank 134 in the guide opening 130 and for the other part by way of the spring 122 supported both on the electrically conductive housing 132 all round the opening 130 and also on the inner thickened end of the part 164. The housing 132 is electrically insulated from the head 154 through an insulating plate 136. The contact plate 128 is secured within the housing 132 with spacing therefrom on the insulating plate 136, and accordingly electrically insulated from the housing 132. If now a correspondingly great torque is exerted upon the free end of the plate displacement part 164 in the displacement of the part 170 carrying the housing 132 (corresponding to the part 70 in FIG. 2) in the direction D', then the inner end of the plate displacement part 164 slides from the seating 124 and is then pressed by the spring 122 against the contact plate 128. If now the contact plate 128 and the housing 132 are parts of a current circuit, this hitherto open circuit will now be closed by the plate displacement part 122. This can be used for switching off the motor 62. In FIG. 7 there is seen a control system, represented as block 140, for the motor 62 which is conductively connected through a connection lead 142 with the housing 132 and through a connection lead 144 with the contact plate 128. In the case of overload, to which reference has been made, the control system ensures switching off of the motor 62.

By reason of the rotationally symmetrical arrangement of contact plate 122, conical insulating part 126, plate displacement part 122 and housing 132, closure of the current circuit results even when the plate displacement part 164 is overloaded in another direction, for example when, in a vertical movement of the head 40, the plate displacement part 164 strikes against any obstacle, for example one of the counter-projections 78 of pin form. The control system 140 consequently switches off both motors 60 and 62.

We claim:

1. Apparatus for performing chemical reactions, comprising:
    a stack (12) of reaction plates arranged one above another in a stacking direction, said plates being movable relative to one another in a stepwise manner for a constant-stepping interval (a) in a moving direction perpendicular to said stacking direction, each of said plates being provided with passages arranged at mutual distances according to the stepping interval (a), one of said passages of each of said plates being enlarged to form a reaction chamber;
    a plate moving means (56) for the stepwise movement of any one of said plates in said moving direction, said plate moving means including a movable head arranged along side said stack (12) and means for moving said head in said stacking direction from plate to plate between two first end positions, in one of said first end positions the head confronts an outermost plate at one end of said stack, and in the other of said first end positions the head confronts an outermost plate of another end of said stack, said plate moving means further including a plate moving part (64) mounted on said head (54) and provided for mutual engagement with and stepwise movement of a respective one of said plates of the stack, which is confronted by the head in said moving direction and means for moving said plate moving part stepwise in said moving direction; and
    a stack clamping means for applying a compression force parallel to said stacking direction onto said stack in order to sealingly clamp said plates of said stack together, said stack clamping means including a pressing part (100) movable between a compression position and a release position, in said compression position the pressing part (100) urges against one end of the stack with said compression force, and in said release position the pressing part (100) does not urge said one end of said of said stack so as to allow stepping movement of said plate (16) in said moving direction, said head (54) being movable beyond one of said first end positions into a second end position, and said clamping means further including a force transmission device coupled between said head (54) and said pressing part (100) so that upon movement of said head from said one of said first end positions into said second end position, said pressing part is moved automatically from said release position into said compression position, and vice versa.

2. Apparatus according to claim 1, wherein the force transmission device comprises a two-armed level (80) of which one end co-operates with the head (54) and another end co-operates with the pressing part (100).

3. Apparatus according to claim 2, wherein at least one of the ends of the two-armed level (80) is provided with a clamping pressure adjusting device.

4. Apparatus according to claim 3, wherein the clamping pressure adjusting device is formed by an adjustable double wedge (94).

5. Apparatus according to claim 2, wherein the head (54) of the plate moving means (56) is provided on its upper side with a projection (97) which, on a movement of the head (54) beyond said one of said first end positions into said second end position acts on the one end of the two-armed level (80).

6. Apparatus according to claim 1, wherein O-ring seals (26, 34) between successive plates (14) are provided for sealing the passages (16) to the exterior.

7. Apparatus according to claim 1 wherein liquid is fed to the passages (16) of the stack (12) by way of a mixer valve arrangement (51).

8. Apparatus according to claim 1, wherein each of said plates is elongated and has an axis of elongation parallel to the axis of elongation of the other plates and normal to said stacking direction.

9. Apparatus for performing chemical reactions, comprising:
    a stack (12) of reaction plates arranged one above another in a stacking direction, said plates being movable relative to one another in a stepwise manner for a constant stepping interval (a) in a moving direction perpendicular to said stacking direction, each of said plates being provided with passages arranged at mutual distances according to the stepping interval (a), one of said passages of each of said plates being enlarged to form a reaction chamber;
    a plate moving means (56) for the stepwise movement of any one of said plates in said moving direction, said plate moving means including a movable head arranged along side said stack (12) and means for moving said head in said stacking direction from plate to plate between two first end positions, in one of said first end positions the head confronts an outermost plate at one end of said stack, and in the other of said first end positions the head confronts an outermost plate of another end of said stack, said plate moving means further including a plate moving part (64) movably mounted on said head (54) and provided for mutual engagement with and stepwise movement of a respective one of said plates of the stack, which is confronted by the head in said moving direction, means for moving said plate moving part stepwise in said moving direction; and
    a stack clamping means for applying a compression force parallel to said stacking direction onto said stack in order to sealingly clamp said plates of said stack together, said stack clamping means including a pressing part (100) movable between a compression position and a release position, in said compression position the pressing part (100) urges against one end of the stack with said compression force, and in said release position the pressing part (100) does not urge said one end of said of said stack so as to allow stepping movement of said plate (16) in said moving direction, a shift lock means being provided which, during movement of one of said plates by said plate moving part (64) locks one of the neighboring plates of said moving plates against movement in said moving direction, said shift lock means being mounted on said head (54).

10. Apparatus according to claim 9, wherein the shift lock means is constructed so as to lock simultaneously both neighboring plates of said moving plate.

11. Apparatus according to claim 10, wherein said shift lock means includes tow engagement elements (52) rigidly mounted on the head (54) so as to engaged with a counter-engagement element provided on each of said both neighboring plates (14).

12. Apparatus according to claim 11, wherein one of the engagement element and counter-engagement element comprises an engagement projection (50, 52), the other of the elements comprises a plurality of engagement grooves (72) arranged one after another in the moving direction at the stepping interval, extending parallel to the stacking direction and constructed for the receipt of the engagement projection.

13. Apparatus according to claim 11, wherein one of the engagement element and counter-engagement element comprises an engagement groove extending parallel with the stacking direction, the other of the elements comprises a plurality of engagement projections arranged one after another in the moving direction at the stepping interval (a) and constructed for insertion into any one of said grooves.

14. Apparatus according to claim 12, wherein a pressure application part (100) provided at one end of said stack is formed with an additional engagement groove (98) constructed for the receipt of the engagement projection (52).

15. Apparatus according to claim 9, wherein each of said plates is elongated and has an axis of elongation parallel to the axis of elongation of the other plates and normal to said stacking direction.

16. Apparatus for performing chemical reactions, comprising:
a stack (12) of reaction plates arranged one above another in a stacking direction, said plates being movable relative to one another in a stepwise manner for a constant stepping interval (a) in a moving direction perpendicular to said stacking direction, each of said plates being provided with passages arranged at mutual distances according to the stepping interval (a), one of said passages of each of said plates being enlarged to form a reaction chamber;
a plate moving means (56) for the stepwise movement of any one of said plates in said moving direction, said plate moving means including a movable head arranged along side said stack (12) and means for moving said head in said stacking direction from plate to plate between two first end positions, in one of said first end positions the head confronts an outermost plate at one end of said stack, and in the other of said first end positions the head confronts an outermost plate of another end of said stack, said plate moving means further including a plate moving part (64) movably mounted on said head (54) and provided for mutual engagement with and stepwise movement of a respective one of plates of the stack, which is confronted by the head in said moving direction and means for plate moving said plate moving part stepwise in said moving direction; and
a stack clamping means for applying a compression force parallel to said stacking direction onto said stack in order to sealingly clamp said plates of said stack together, said stack clamping means including a pressing part (100) movable between a compression position and a release position, in said compression position the pressing part (100) urges against one end of the stack with said compression force, and in said release position the pressing part (100) does not urge said one end of said of said stack so as to allow stepping movement of said plate (16) in said moving direction, the plate moving part including a projection (76) mounted onto a carrier part (170), said carrier part (170) being movable in said moving direction relative to said head by said plate moving part moving means of said plate moving means, said projection (76) cooperating selectivity with a counter projection (78) formed on each of said plates (14).

17. Apparatus according to claim 16, wherein the moving projection (76), in an intermediate position of the head (54) between successive plate moving positions of said head, is movable freely between the counter-projections (78) of successive plates (14).

18. Apparatus according to claim 16, wherein at least one of the moving projection (76) and the counter-projections (78) is of pin form.

19. Apparatus according to claim 16, wherein the plate moving part (164) includes an overload safety means for preventing damage to said plates moving part when engaging a respective one of said plates.

20. Apparatus according to claim 19, wherein the plate moving part (164) is an electrically conductive pin and is movable between a normal position and an overload position, and wherein a spring element (122) is provided, said spring element (122) urging said moving part (164) against an isolating part (126) in said normal position of said moving part (164) and against an electrically conductive control plate (128) in said overload position of said plate moving part (164).

21. Apparatus according to claim 16, wherein each of said plates is elongated and has an axis of elongation parallel to the axis of elongation of the other plates and normal to said stacking direction.

* * * * *